(12) United States Patent
Heni et al.

(10) Patent No.: US 11,950,761 B2
(45) Date of Patent: Apr. 9, 2024

(54) AUTOCLAVABLE KEYPAD WITH HAPTIC FEEDBACK FOR VIDEO ENDOSCOPES

(71) Applicant: KARL STORZ SE & Co. KG, Tuttlingen (DE)

(72) Inventors: Pascal Heni, Fridingen (DE); Daniel Ulmschneider, Nendingen (DE); Markus Kupferschmid, Emmingen-Liptingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 18/062,798

(22) Filed: Dec. 7, 2022

(65) Prior Publication Data

US 2023/0096366 A1    Mar. 30, 2023

Related U.S. Application Data

(63) Continuation of application No. 17/187,426, filed on Feb. 26, 2021, now Pat. No. 11,550,402.

(30) Foreign Application Priority Data

Feb. 27, 2020 (DE) ...................... 10 2020 105 238.3

(51) Int. Cl.
*G06F 3/02* (2006.01)
*A61B 1/00* (2006.01)

(52) U.S. Cl.
CPC ...... *A61B 1/00042* (2022.02); *A61B 1/00039* (2013.01); *A61B 1/00066* (2013.01); *G06F 3/0219* (2013.01)

(58) Field of Classification Search
CPC ............ A61B 1/00042; A61B 1/00039; A61B 1/00066; G06F 3/0219; H01H 13/48
See application file for complete search history.

(56) References Cited

U.S. PATENT DOCUMENTS

2011/0216008 A1 * 9/2011 Adams ................ H01H 13/705 29/622
2019/0083882 A1 * 3/2019 Soelberg ................ G06F 3/016

FOREIGN PATENT DOCUMENTS

JP    2004288459 A  * 10/2004

* cited by examiner

*Primary Examiner* — Adam R. Giesy
(74) *Attorney, Agent, or Firm* — David N. Villalpando

(57) ABSTRACT

A keypad includes a support, a snap disk on a first side of the support transformable from a released state to a loaded state, a cover forming a seal over the first side, a pocket in the cover, a magnet and a plunger disposed in the pocket, the plunger adapted to engage and transform the snap disk to the loaded state, a magnetic field sensor on a second side of the support, the second side opposite the first side and logic circuitry adapted to obtain a value of a strength of a magnetic field from the sensor, compare the value against a predetermined threshold value that corresponds at least approximately to the strength of a magnetic field, and when the plunger has transformed the snap disk to the loaded state and the value reaches or exceeds the threshold value, output a signal indicating that a key press occurred.

18 Claims, 1 Drawing Sheet

AUTOCLAVABLE KEYPAD WITH HAPTIC FEEDBACK FOR VIDEO ENDOSCOPES

CROSS-REFERENCE TO RELATED APPLICATIONS

This application is a continuation of U.S. patent application Ser. No. 17/187,426, filed on Feb. 26, 2021, and entitled "Autoclavable Tactile Keypad for Video Endoscopes," now U.S. Pat. No. 11,550,402, issued on Jan. 10, 2023, which in turn claims priority to German Patent Application No. 10 2020 105 238.3, filed Feb. 27, 2020, and entitled "Tastatur für ein Endoskop and Endoskop mit Tastatur." The content of both these applications are incorporated herein by reference in its entirety.

FIELD

The present disclosure relates to a keypad for an endoscope comprising a logic circuitry and plurality of keys arranged under an elastic watertight cover and an endoscope with such a keypad.

BACKGROUND

Keypads in the medical environment are faced with a number of challenges that are unknown to conventional keypads, for example allowing for a rigorous cleaning and avoiding room for the settling of contaminations. Also, especially for endoscopes, the pressing of a key on the keypad may not always have an immediately visible effect, so that it must be ensured that when, from the perception of the user, a key is pressed the corresponding instrument responds in a corresponding manner.

Therefore, it is an object to provide an improved keypad that can be used for an endoscope in a medical environment, especially a sterile environment, that is highly reliable in its functionality and in responding to the control exerted by the user. Also, it is desired that the manufacturing of the keypad can still be achieved in an effective manner. A further object is to provide a corresponding endoscope.

SUMMARY

A keypad for an endoscope includes logic circuitry, an elastic watertight cover including an undercut pocket, a support; and a plurality of keys arranged under the elastic watertight cover. Each key includes an actuator section arranged over the support and a sensor section arranged below the support. The actuator section includes a magnet held in the undercut pocket in the cover, wherein the magnet is held over a snap disk. The sensor section includes a sensor adapted to detect a strength of a magnetic field of the magnet at the sensor. The actuator section is adapted to, when the key is pressed by a user, press against the snap disk and transform the snap disk from a released state into a loaded state. The actuator section is further adapted to, when the key is released by the user, move away from the snap disk to allow the snap disk to return from the loaded state back to the released state. The logic circuitry is adapted to obtain a value of the strength of the magnetic field from the sensor, compare the value against a predetermined threshold value that corresponds at least approximately to the strength of a magnetic field when the actuator section has transformed the snap disk, and output a signal indicating that the key is pressed when the value reaches or exceeds the threshold value.

In other features, the cover includes rests that are arranged on the support and the pocket is held between the rests elevated over the snap disk by at least one stand.

In other features, the actuator section includes a plunger adapted to press onto the snap disk. The plunger has a cross-section with a T-shape, and a vertical bar of the T-shape is adapted to press onto the snap disk. In still other features, the plunger is arranged below the magnet. In yet other features, the magnet comprises a hollow shaft in which a section of the plunger is arranged. In other features, the plunger is held in the pocket. In still other features, the plunger is adapted to press at least substantially onto a center of the snap disk. In yet other features, the plunger is glued to a bottom side of the magnet that faces the snap disk.

In other features, the cover is autoclavable, the sensor is a Hall-sensor, the support is adapted to fully separate the actuator section from the sensor section, the cover is made of a single piece of silicone, and the snap disk is attached to the support via an adhesive tape that is adhesive on both sides.

One feature of this keypad is that the snap disk gives a good haptic feedback when the user presses a key on the keypad. Further, sensing the magnet's magnetic field allows to separate the actuator section from the sensor section. Also, holding the magnet in the pocket that is formed as an undercut in the cover, allows to hold the magnet in place without the need for adhesives, thus simplifying the manufacturing process.

DETAILED DESCRIPTION

Figure 1:
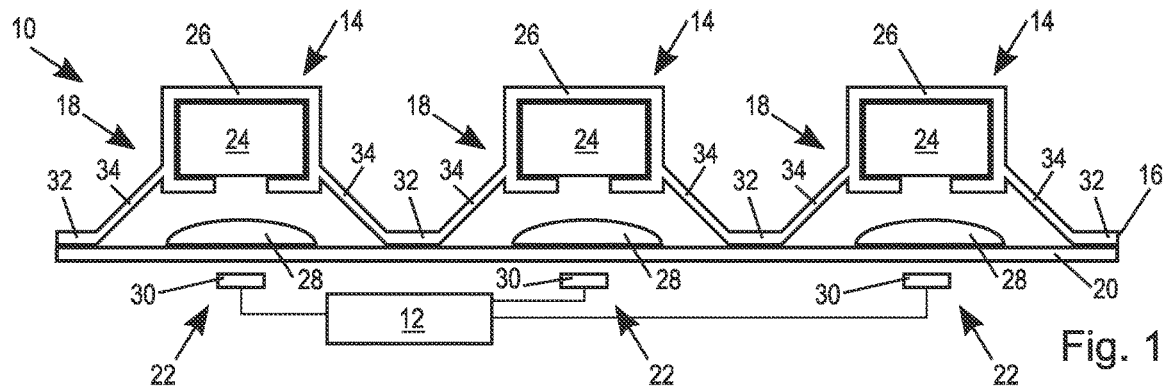
FIG. 1 a first embodiment of a keypad in a cross-sectional view.

FIG. 1 shows a first embodiment of a keypad 10 for an endoscope in a cross-sectional view. The keypad 10 comprising a logic circuitry 12 and plurality of keys 14 arranged under an elastic watertight cover 16. As used herein, endoscope includes video endoscopes and optical endoscopes with attached camera heads. The endoscopes may be flexible or rigid shaft endoscopes and used for a variety of medical purposes.

Each key 14 comprises an actuator section 18 arranged over a support 20 and a sensor section 22 arranged below the support 20. The actuator section 18 comprises a magnet 24 held in an undercut pocket 26 in the cover 16. The magnet 24 is held over a snap disk 28.

The sensor section 22 comprises a sensor 30 adapted to detect a strength of a magnetic field of the magnet 24 at the sensor 30. The actuator section 18 is adapted to, when the key 14 is pressed by a user, here in a downward direction, to press against the snap disk 28 and transform the snap disk 28 from a released state into a loaded state. Further, the actuator section 18 is adapted to, when the key 14 is released by the user, here in an upward direction, move away from the snap disk 28 to allow the snap disk 28 to return from the loaded state back to the released state.

The logic circuitry 12 is adapted to obtain a value of the strength of the magnetic field from the sensor 30, to compare the value against a predetermined threshold value. This predetermined threshold value corresponds at least approximately to the strength of a magnetic field when the actuator section 18 has transformed the snap disk 28. The logic circuitry 12 is further adapted to output a signal indicating that the key 14 is pressed, when the value reaches or exceeds the threshold value.

The cover 16 comprises rests 32 that are arranged on the support 20 and the pocket 26 is held between the rests 32 elevated over the snap disk 28 by at least one stand 34. In some embodiments the at least one stand 34 has the shape of a frustum.

Figure 2:
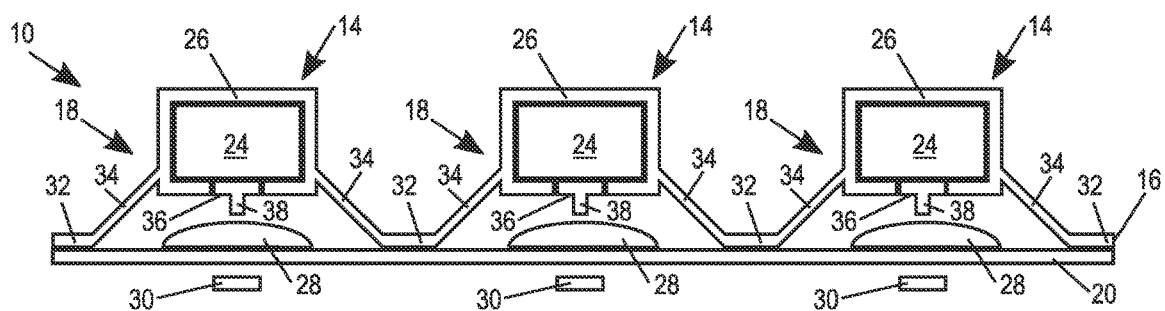
FIG. 2 a second embodiment of a keypad in a cross-sectional view.

FIG. 2 shows a first embodiment of a keypad 10 for an endoscope in a cross-sectional view. All previously introduced reference numerals are maintained. The previously given explanations concerning the structure of the keypad 10 apply to this embodiment as well. The logic circuitry 12 is present as well but is not shown here.

Different from the first embodiment, the actuator section 18 comprises a plunger 36 adapted to press onto the snap disk 28. The plunger 36 may be glued to a bottom side of the magnet 24. The plunger 36 achieves a well-defined contact with the snap disk 28 which allows to achieve a well-defined click when the snap disk 28 is transformed from the released state into the bent state and also when released back into the released state.

As shown, the plunger 36 has a cross-section with a T-shape, and wherein a vertical bar 38 of the T-shape is adapted to punctually press onto the snap disk. More specifically, the plunger 36 is adapted to press at least substantially onto a center of the snap disk 28. The plunger 36 may be symmetrical around the vertical bar 38, in particular like a tack.

Figure 3:
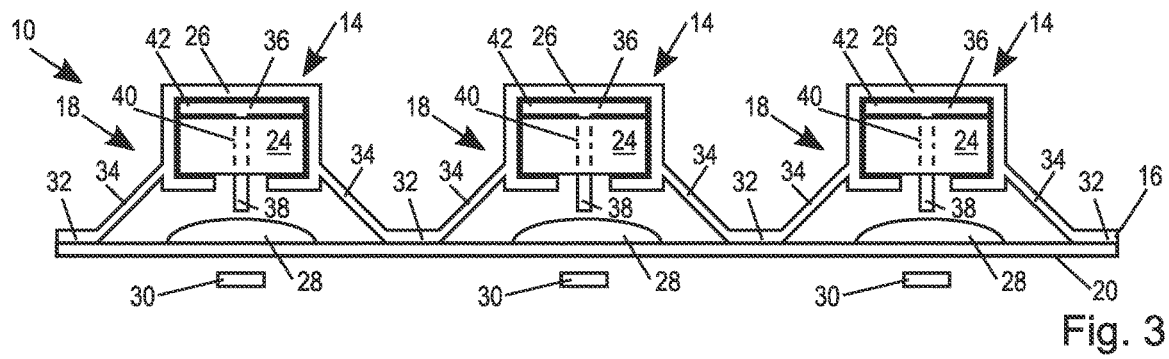
FIG. 3 a third embodiment of a keypad in a cross-sectional view.

FIG. 3 shows a third embodiment of a keyboard 10 for an endoscope in a cross-sectional view. All previously introduced reference numerals are maintained. The previously given explanations concerning the structure of the keyboard 10 apply to this embodiment as well. The logic circuitry 12 is present as well but is not shown here.

Different from the second embodiment, the magnet 24 comprises a hollow shaft 40, indicated with the dashed line, in which a section of the plunger 36 is arranged. A horizontal bar 42 of the T-shape rests on the magnet 24. This gives a good contact between the user's finger and the plunger 36, so that a good haptic feedback is provided to the user, especially when transforming the snap disk 28, i.e. clicking the snap disk 28.

Figure 4:
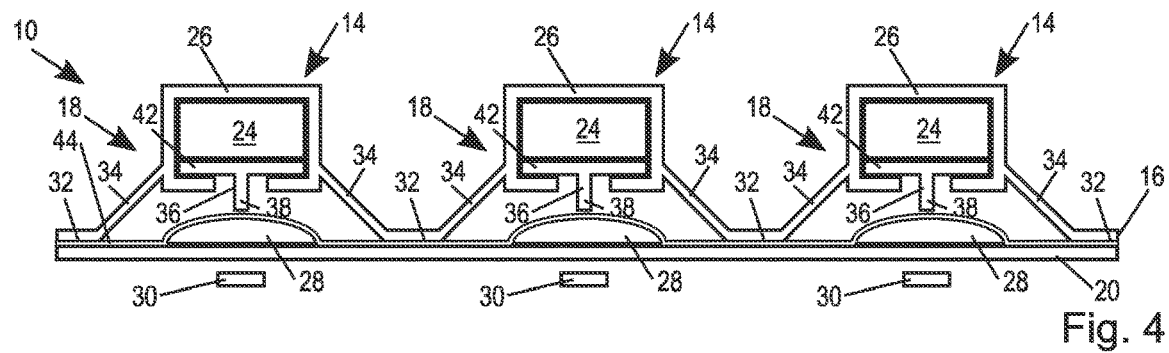
FIG. 4 a fourth embodiment of a keypad in a cross-sectional view.

FIG. 4 shows a fourth embodiment of a keyboard 10 for an endoscope in a cross-sectional view. All previously introduced reference numerals are maintained. The previously given explanations concerning the structure of the keyboard 10 apply to this embodiment as well. The logic circuitry 12 is present as well but is not shown here.

Different from the second embodiment, the plunger 36 is arranged below the magnet 24 and held in the pocket 26. There is no need to attach the plunger 36 to the magnet 24 as the plunger 36 is held in the pocket 26 with the magnet 24. Also, in comparison to the third embodiment, the structure of the magnet 24 may be kept simpler as no hollow shaft 40 is required.

Reference made throughout the specification to endoscopes include video endoscopes in which image sensors are placed at a distal end of the endoscope and controls such as the keypad are disposed at the proximal end. However, endoscopes may also include optical endoscopes with camera heads coupled at the proximal end. Both video endoscopes and camera head-style optical endoscopes commonly employ keypads for control. Thus, the principles of the present disclosure may be applied to both.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

The invention claimed is:

1. A keypad including one or more keys for an endoscopic instrument, comprising:
   a support;
   a snap disk on a first side of the support and transformable from a released state to a loaded state;
   a cover forming a seal over the first side to prevent fluids entering;
   an undercut pocket in the cover;
   a magnet disposed in the pocket;
   a plunger disposed in the pocket, wherein the plunger is adapted to engage the snap disk to transform the snap disk to the loaded state, where at least one portion each of the magnet, the plunger, and the snap disk, are in vertical alignment;
   a magnetic field sensor on a second side of the support, the second side opposite the first side; and
   logic circuitry adapted to
     obtain a value of a strength of a magnetic field from the sensor,
     compare the value against a predetermined threshold value that corresponds at least approximately to the strength of a magnetic field,
     and when the plunger has transformed the snap disk to the loaded state and the value reaches or exceeds the threshold value, output a signal indicating that a key press occurred.

2. The keypad of claim 1, wherein the cover comprises rests that are arranged on the support and the pocket is held between the rests elevated over the snap disk by at least one stand.

3. The keypad of claim 1, wherein the plunger has a cross-section with a T-shape, and wherein a vertical bar of the T-shape is adapted to press onto the snap disk.

4. The keypad of claim 1, wherein the plunger is arranged below the magnet.

5. The keypad of claim 1, wherein the magnet comprises a hollow shaft in which a section of the plunger is arranged.

6. The keypad of claim 1, wherein the plunger is held in the pocket.

7. A keypad for an endoscope, comprising
   a logic circuitry;
   an elastic watertight cover including an undercut pocket;
   a support; and
   a plurality of keys arranged under the elastic watertight cover, each key comprising an actuator section arranged over the support and a sensor section arranged below the support,
  the actuator section comprising a magnet held in the undercut pocket in the cover, wherein the magnet is held vertically above and horizontally aligned with at least a portion of a snap disk, and the actuator section further comprising a plunger comprising the magnet, the plunger adapted to press onto the snap disk, and
  the sensor section comprising a sensor adapted to detect a strength of a magnetic field of the magnet at the sensor,
wherein the actuator section is adapted to press against the snap disk and transform the snap disk from a released state into a loaded state when the key is pressed by a user and is adapted to move away from the snap disk to allow the snap disk to return from the loaded state back to the released state when the key is released by the user, and
wherein the logic circuitry is adapted to
  obtain a value of the strength of the magnetic field from the sensor,
  compare the value against a predetermined threshold value that corresponds at least approximately to the strength of a magnetic field when the actuator section has transformed the snap disk, and
  output a signal indicating that the key is pressed when the value reaches or exceeds the threshold value.

8. The keypad of claim 7, wherein the cover comprises rests that are arranged on the support and the pocket is held between the rests elevated over the snap disk by at least one stand.

9. The keypad of claim 7, wherein the plunger comprises the undercut pocket in the cover.

10. The keypad of claim 7, wherein the portion of the plunger adapted to press into the snap disk is arranged below the magnet.

11. The keypad of claim 7, wherein the plunger has a cross-section with a T-shape, and wherein a vertical bar of the T-shape is adapted to press onto the snap disk.

12. The keypad of claim 7, wherein the magnet comprises a hollow shaft in which a section of the plunger is arranged.

13. The keypad of claim 7, wherein the plunger is held in the pocket.

14. The keypad of claim 7, wherein the plunger is adapted to press at least substantially onto a center of the snap disk.

15. The keypad of claim 7, wherein the cover is autoclavable.

16. The keypad of claim 7, wherein the sensor is a Hall-sensor.

17. The keypad of claim 7, wherein the support is adapted to fully separate the actuator section from the sensor section.

18. The keypad of claim 7, wherein the cover is made of a single piece of silicone.

* * * * *